United States Patent
Hronec

(10) Patent No.: US 8,987,528 B2
(45) Date of Patent: Mar. 24, 2015

(54) METHOD OF HYDROGENOLYSIS OF SUGAR ALCOHOLS

(75) Inventor: Milan Hronec, Bratislava (SK)

(73) Assignee: Mossi & Ghisolfi International S.a.r.l., Luxembourg (LU)

( * ) Notice: Subject to any disclaimer, the term of this patent is extended or adjusted under 35 U.S.C. 154(b) by 358 days.

(21) Appl. No.: 13/262,675

(22) PCT Filed: Jan. 27, 2010

(86) PCT No.: PCT/IB2010/050358
§ 371 (c)(1),
(2), (4) Date: Oct. 3, 2011

(87) PCT Pub. No.: WO2010/119351
PCT Pub. Date: Oct. 21, 2010

(65) Prior Publication Data
US 2012/0029249 A1 Feb. 2, 2012

(30) Foreign Application Priority Data

Apr. 16, 2009 (WO) .................. PCT/IT2009/000166

(51) Int. Cl.
| | |
|---|---|
| *C07C 29/153* | (2006.01) |
| *B01J 29/12* | (2006.01) |
| *B01J 23/46* | (2006.01) |
| *B01J 37/02* | (2006.01) |
| *C07C 29/00* | (2006.01) |
| *B01J 21/18* | (2006.01) |

(52) U.S. Cl.
CPC .............. *B01J 29/126* (2013.01); *B01J 23/466* (2013.01); *B01J 37/0203* (2013.01); *C07C 29/00* (2013.01); *B01J 21/18* (2013.01)
USPC ............................ 568/863; 568/852; 568/864

(58) Field of Classification Search
USPC .......................... 568/852, 863, 864; 536/124
See application file for complete search history.

(56) References Cited

U.S. PATENT DOCUMENTS

| | | | |
|---|---|---|---|
| 5,026,927 A | 6/1991 | Andrews et al. | |
| 6,291,725 B1 * | 9/2001 | Chopade et al. | ............... 568/861 |
| 2003/0139535 A1 * | 7/2003 | Haga et al. | ................ 525/338 |
| 2007/0123739 A1 * | 5/2007 | Crabtree et al. | ............... 568/863 |

FOREIGN PATENT DOCUMENTS

| | | |
|---|---|---|
| WO | 03/035593 A | 5/2003 |
| WO | 2005/051874 A | 6/2005 |

\* cited by examiner

*Primary Examiner* — Sudhakar Katakam
*Assistant Examiner* — Pancham Bakshi
(74) *Attorney, Agent, or Firm* — Edwin A. Sisson, Attorney at Law, LLC

(57) ABSTRACT

The method for hydrogenolysis of sugar or sugar alcohols comprises the steps of: mixing in the absence of any phosphine a suspension of a supported osmium catalyst, water, a sugar or sugar alcohol, and a base; pressurizing the suspension with hydrogen to a range of 30 to 90 bar at room temperature; heating the suspension to a temperature in the range of 180° C. to 250° C.; and mixing the suspension for an amount of time ranging from 1 to 6 hours.

8 Claims, No Drawings

METHOD OF HYDROGENOLYSIS OF SUGAR ALCOHOLS

PRIORITY AND CROSS REFERENCES

This patent application claims the priority from PCT/IB2010/050358 (IB) filed 27 Jan. 2010; and PCT/IT2009/000166 (IT) filed 16 Apr. 2009.

BACKGROUND OF THE INVENTION

There is a great deal of information in the literature, mostly in patents, concerning catalytic hydrogenolysis of sugars or sugar alcohols into mixtures of polyols, for example, glycerol, ethylene and propylene glycols. Hydrogenolysis involves the cracking of a carbon to carbon linkage in a molecule with the simultaneous addition of hydrogen to each of the fragments produced by the cracking. The hydrogenolysis of sugars and higher polyols has multiple steps. The polyol is first dehydrogenated by a catalyst to an aldehyde or a ketone. The product of dehydrogenation undergoes either a C—C or a C—O cleavage. The overall reaction sequence leading to C—C cleavage or C—O cleavage, which occurs by dehydration, is affected by a metal catalyst and a base and goes through a number of intermediates. The metal catalyst is both a hydrogenating and a dehydrogenating catalyst.

Catalysts based on Ir, Ni, Rh and especially Ru are active but poorly selective because they excessively hydrogenolyse C—C and C—O bonds. Modification of these metals by additives often leads to significant changes in selectivities. As an example, Ru catalyst after modification with sulfur compounds (sodium sulfide) and in the presence of a base (Ca$(OH)_2$) at 250° C. under 140 bar of hydrogen, is able to convert 98% of glucitol into 91% of a mixture of ethylene glycol (26%) and 1,2-propanediol (65%) (U.S. Pat. No. 4,430,253).

Tin has a similar effect as sulfur compounds on the modification of ruthenium catalysts, preferably in the atomic ratio Ru/Sn from 2 to 1 (G. Gubitosa and B. Casale. U.S. Pat. No. 5,354,914). Hydrogenolysis of higher polyhydric alcohols in the presence of Ru/Sn catalyst increases the selectivity towards the production of lower polyhydric alcohols and keeps the formation of undesired products such as gaseous hydrocarbons to a minimum. A certain advantage of tin modified Ru catalyst is that the quantity of the catalyst required to reach conversion of polyhydric alcohols, comparable to sulfur—modified Ru catalyst, is several times lower.

U.S. Pat. No. 5,210,335 describes the preparation of lower polyhydric alcohols by catalytic hydrogenolysis of sucrose in an aqueous solution using a catalyst whose active material in the unreduced form essentially consists of 66.8 wt % of CoO, 19.2 wt % of CuO, 7.1 wt % of $Mn_3O_4$, 3.4% $H_3PO_4$ and 3.5% of $MoO_3$. The hydrogenolysis reaction proceeds at reaction temperatures of 250° C. and pressures from 280 to 300 bar for 4.5 hours of a total reaction time. The reaction mixture contains 60 wt % of propylene glycol, 20 wt % of ethylene glycol and the rest other mono-, di-, tri- and tetrahydric alcohols. The conversion of sucrose is total.

U.S. Pat. Nos. 5,214,219 and 5,616,817 use mixed-oxide catalysts Co—Zn and Co—Cu—Mn—Mo for hydrogenolysis of glycerol to ethylene and propylene glycols.

The increased selectivity of hydrogenolysis of sugars or polyhydric alcohols to desired products such as ethylene and propylene glycols is also achieved by using the synergistic effect of various multimetallic catalysts, for example Ni—Re (U.S. Pat. Nos. 6,841,085 and 7,038,094), Ni—W—Cu, and Ni—Mo—Cu.

Metallic catalysts are obviously supported on carriers. The type of carrier (e. g. acid-base properties), its texture (surface area, porosity) and the dispersion of metals are also very important factors influencing the activity of the catalyst and the selectivity of the hydrogenolysis process. For example, the preferred support for the ruthenium catalyst is microporous carbon (U.S. Pat. No. 6,291,725).

A homogeneous process has also been described (WO 2005/051874). The reaction proceeds in the homogeneous liquid phase in the presence of a homogeneous ruthenium or osmium catalyst coordinated with tridentate phosphines to give a sugar conversion in an excess of 90% with greater than 70% selectivity to ethylene and propylene glycols. Good results may be obtained at a pressure below 70 bar. As indicated, the reaction process of WO 2005/051874 must necessarily proceed in homogeneous liquid phase, wherein the catalyst is fully dissolved and not merely suspended. Only after such reaction process, when the catalyst is removed from the reactor, it can be possibly immobilized on a support to assist its recovery.

The hydrogenolysis process is conveniently carried out in an aqueous reaction medium. However, a variety of other solvents may be employed. Alternative solvents include, e.g., ethylene glycol, $C_1$-$C_4$ monohydric alcohols, especially methanol. Use of protic solvents results in a higher conversion to ethylene glycol than does use of e.g. cyclohexane (U.S. Pat. No. 4,404,411).

It is important to maintain the pH range during the hydrogenolysis process. Maintaining the pH within the preferable range 9.0 to 11. (U.S. Pat. No. 4,476,331) is important to achieve product selectivity. Useful basic materials include alkali metal hydroxides and basic salts.

There exists therefore a need for a heterogenous catalyst with high activity and selectivity that can be, without reactivation, recycled back through the hydrogenolysis process without losing activity and selectivity. Such a recyclable catalyst would enable high yields of lower glycols at milder reaction conditions, and with a lower concentration of catalyst. Such a catalyst, is heretofore unreported in the literature.

SUMMARY OF THE INVENTION

It remained for the present inventor to recognize that a catalyst composition and method could be devised with particular embodiments to allow a heterogeneous, recyclable catalyst with high activity and selectivity. Such a catalyst enables high yields of lower glycols at milder reaction conditions, and with a lower concentration of catalyst. This specification discloses such a method for hydrogenolysis of sugar alcohols in the absence of any phosphine comprising the steps of mixing a suspension of a supported osmium catalyst, water, a sugar alcohol, and a base, pressurizing the suspension with hydrogen to a range of 30 to 90 bar at room temperature, heating the suspension to a temperature in the range of 180° C. to 250° C., and mixing the suspension for an amount of time ranging from 1 to 6 hours.

Further disclosed in the specification is a method for hydrogenolysis of sugar alcohols wherein the sugar alcohol is sorbitol.

Further disclosed in the specification is a method for hydrogenolysis of sugar alcohols comprising the steps of mixing a suspension of a supported osmium catalyst, water, a sugar alcohol, and a base, wherein the base is selected from the group of alkali metals, alkaline earth metals or mixtures thereof.

Further disclosed in the specification is a method for hydrogenolysis of sugar alcohols comprising the steps of mixing a suspension of a supported osmium catalyst, water, a sugar alcohol, and a base, wherein the base is barium hydroxide.

Further disclosed in the specification is a method for hydrogenolysis of sugar alcohols comprising the steps of mixing a suspension of a supported osmium catalyst, water, a sugar alcohol, and a base, in which at least some of the supported osmium catalyst is recovered and reused for the hydrogenolysis of sugar alcohols.

Contrary to the suggestions of the prior art, the method for hydrogenolysis of sugar alcohols according to the present invention uses a supported Os catalyst, exempt from Ru and phosphines and suspended in the reaction medium and thus provides for an heterogeneous reaction process. Surprisingly, in these conditions, such Os catalyst exhibits higher activity, namely higher conversions of sugars, and higher selectivity of formation of lower diols, especially propylene glycol, at lower reaction temperatures and hydrogen pressures.

This specification also discloses a highly active and selective catalyst composition for the hydrogenolysis of sugar alcohols, wherein the catalyst composition comprises an osmium precursor, and a support.

Still another feature involves a highly active and selective catalyst composition for the hydrogenolysis of sugar alcohols, wherein the catalyst composition comprises an osmium precursor, and a support in which the osmium precursor is OsO4 or OsCl3.

Still another feature involves a highly active and selective catalyst composition for the hydrogenolysis of sugar alcohols, wherein the catalyst composition comprises an osmium precursor, and a support in which the support is activated carbon.

DETAILED DESCRIPTION

The present invention relates to an improvement in a process for the production of lower glycols by the hydrogenolysis of sugar and sugar alcohols using a supported osmium catalyst. The sugar alcohol starting material can be monosaccharides, disaccharides or a mixture thereof. Monosaccharides include glucose, fructose, galactose, arabinose, ribose and xylose. Disaccharides that can be converted into lower glycols include e.g. sucrose, maltose, and lactose. Mixtures of monosaccharides and disaccharides can also be hydrogenolyzed. The present process of sugar alcohols hydrogenolysis is conveniently carried out in an aqueous medium. The starting material to be hydrogenolyzed may be dissolved in water, but it is not necessary to form the true solution with the water. Suspensions or colloidal suspensions of sugar alcohols react too. Concentrations of sugar alcohols from about 12% to about 40% by weight are usually employed for the reaction.

According to the present invention, a supported osmium catalyst is used to obtain suitable conversion of starting materials to the desired products. The heterogeneous osmium catalyst intended for hydrogenolysis reaction may be prepared using various techniques, e.g. impregnation, precipitation, vaporization, sol-gel method, microemulsion method, etc. The concentration of the osmium on the support is between 0.5 and 10 wt. % and preferably between 1 and 6 weight %. The osmium precursor may be in the form of a cation, an anion, a complex compound or ligand deficient clusters stabilized by a small amount of carbonaceous ligands. A precursor may be in liquid or solid form. The support and precursor composition can be mixed in a suspension. An example of an osmium precursor is $OsCl_3$, $OsO_4$ or their solutions or suspensions.

The catalyst support preferably comprises powdered or granulated materials with a high surface area. A higher surface area of metal carriers increases metal dispersion which usually manifested by an increase of catalyst activity. Suitable supports include charcoal, titania, silica, aluminosilicates and the like. The preferred support is carbon prepared from natural sources, e.g. wood, oils or from petroleum residues. The preferred specific surface area of carbons is above 700 $m^2/g$.

Osmium precursor loaded on the surface of the support is prior to use reduced to its metallic state with hydrogen at the temperature from 50° C. up to 300° C. Alternatively, reduction of osmium precursor can be realized in the presence of aqueous solution of starting reactants, sugar alcohols, directly in the reaction mixture placed in a reactor.

The reaction is carried out at a temperature of at least about 180° C. to about 250° C., preferably at 195-225° C. A wide range of pressures can be used. The hydrogen partial pressure at room temperature should be at least about 25 bar, preferably about 30 to 90 bar. The time of reaction depends on the reaction conditions and concentration of reactants and catalyst. Usually, the hydrogenolysis requires about 60 minutes to about 6 hours. The reaction should be continued until the hydrogenolysis is substantially completed. The presence of a suitable base in the reaction medium has a positive effect on the selectivity of hydrogenolysis to lower glycols. Useful basic materials include base selected from the group of alkali metals, alkaline earth metals or their mixtures, e.g. potassium, sodium, calcium, barium in the form of hydroxides, oxides, and carbonates. The amount of base depends on the base selected. The amount of base is preferably within the range of about 0.05 to about 0.2 kg of base per kg of sugar alcohol.

The reaction may be carried out in batch, semi-continuous or continuous operation in reactors that enable intimate contact of the reactants and control of operating conditions. Examples of suitable apparatus include trickle bed, bubble column reactors, slurry reactors and continuous stirred tank. The reactor can be a column with continuous flow through the column of the reaction mixture. The continuous reactor is preferably supplied with a reaction promoter selected from amongst alkali metals, alkaline earth metals or their mixtures.

Upon completion of the hydrogenolysis reaction, the catalyst is removed by filtration or decantation and without washing or reactivation, it can be recycled back to the hydrogenolysis process.

The following examples illustrate the method of making the catalyst and the method of hydrogenolysis.

EXAMPLE 1

For the preparation of the catalyst, activated carbon Norit SX Plus having the following characteristics was used: specific surface area 1080 $m^2/g$, ash content 8 wt %, particle size 0.1-0.2 mm. Before deposition of osmium, the activated carbon was dried at 150° C. overnight. A suspension of $OsO_4$ (0.019 g) and 0.250 g of dried activated carbon in 18 ml of hexane was mixed and treated for 15 h in a 50 ml Teflon lined stainless steel reactor at 130° C. and initial hydrogen pressure of 50 bar. After cooling and opening the reactor the suspension was transferred into the hydrogenolysis reactor and the vessel washed with 10 ml of deionized and de-gassed water. Under nitrogen flux the hydrocarbon phase was evaporated (at about 50° C.). Then into the hydrogenolysis reactor was weighed an additional 7 g of water, 6.0 g of sorbitol and 1.25 g $Ba(OH)_2.8H_2O$. The reactor was closed, 5-times purged with hydrogen and pressurized with hydrogen, to 55 bar. The reaction mixture was slowly mixed and heated to the temperature of 210° C. At this temperature, the reaction mixture was vigorously mixed for 4 hours, then the reactor was cooled, de-pressurized and the gas sample collected for analysis by gas chromatography to ascertain the presence of hydrocarbons and carbon dioxide. The liquid reaction mixture was analyzed by means of high performance liquid chromatography. Under the given reaction conditions, the sorbitol conversion was total and produced a yield of ethylene glycol 11.35 mol % and propylene glycol 51.98 mol %.

EXAMPLE 2

Osmium on zeolite NH4Y was deposited using the incipient wetness method. A quantity of 0.25 g of the zeolite was dried 5 hours at 100° C. in vacuum to remove the trapped water. The aqueous solution of $OsCl_3.xH_2O$ containing 0.013 g Os acidified by hydrochloric acid (1 drop), made up in a volume that was determined to fill the pore volume of the zeolite was added in small portions to the mixing zeolite. The wetted zeolite was placed into the reactor, added 17 g of water, 6.0 g of sorbitol and 0.53 g $Ba(OH)_2.8H_2O$. The reactor was closed, 5-times purged with hydrogen and pressurized with hydrogen, to 55 bar. The reaction mixture was slowly mixed and heated to a temperature of 225° C. At this temperature, the reaction mixture was vigorously mixed for 4 hours, then the reactor was cooled and de-pressurized. Under the given reaction conditions, the sorbitol conversion was 97.8% and produced a yield of ethylene glycol 6.67 mol % and propylene glycol 43.95 mol %

EXAMPLE 3

The catalyst used for this experiment was 3.6% Os on activated carbon Vulcan XC 72 (Cabot Corp.) prepared by the procedure described in Example 1. Into the hydrogenolysis reactor was weighed 0.38 g of this catalyst, 17 g of water, 6.0 g of glucose and 0.57 g $Ba(OH)_2.8H_2O$. The reactor was closed, 5-times purged with hydrogen and pressurized with hydrogen, to 50 bar. The reaction mixture was slowly mixed and heated to the temperature of 210° C. At this temperature, the reaction mixture was vigorously mixed for 3 hours, then the reactor was cooled and de-pressurized. Under the given reaction conditions, the glucose conversion was 94.8% and produced a yield of ethylene glycol 6.19 mol % and propylene glycol 40.35 mol %.

EXAMPLE 4

The catalyst and procedure were the same as in Example 1, except that no base was added. After 5 hours of reaction, the conversion of sorbitol was 92.3% and ethylene glycol and propylene glycol were produced in the yields 5.91 and 9.82 mol %, respectively.

EXAMPLE 5

The catalyst and procedure were the same as in Example 1, except that 0.50 g of KOH, as a base, was used and the reaction temperature 200° C. After 4 hours of reaction, the conversion of sorbitol was total and ethylene glycol and propylene glycol were produced in the yields 8.70 and 37.48 mol %, respectively.

EXAMPLE 6

The catalyst and procedure were the same as in Example 1, except that as a base 0.57 g of $Ba(OH)_2.8H_2O$ was used. The reaction was performed at the reaction temperature 205° C. for 2 hours. The conversion of sorbitol was total and ethylene glycol and propylene glycol were produced in the yields 10.31 and 55.80 mol %, respectively.

EXAMPLE 7

The catalyst and procedure were the same as in Example 3, except that 5.0 g of sucrose was used and the hydrogenolysis reaction was performed at the reaction temperature of 220° C. for 4 hours. Under the given reaction conditions, the sucrose conversion was 92.2% and produced a yield of ethylene glycol 5.60 mol % and propylene glycol 30.21 mol %.

EXAMPLES 8-12

These examples demonstrates the recycling of catalyst. The hydrogenolysis reaction of sorbitol (6.0 g) in water (17 g) was performed in the presence of 0.57 g of $Ba(OH)_2.8H_2O$ at the reaction temperature of 200° C. for 4 hours. The catalyst 5.3% Os on carbon (0.25 g) was prepared according the procedure described in Example 1.

| | | | Yield, mol % | |
|---|---|---|---|---|
| Example | Number of catalyst recycling[a] | Conv. % | Ethylene glycol | Propylene glycol |
| 8 | fresh catalyst | 100 | 11.45 | 54.73 |
| 9 | 1 | 100 | 9.98 | 51.97 |
| 10 | 2 | 100 | 11.84 | 55.33 |
| 11 | 3[b] | 100 | 10.47 | 53.53 |
| 12 | 4 | 100 | 10.27 | 52.57 |

[a] after each catalytic run and settling of the catalyst, the liquid reaction mixture was withdrawn (2-3 ml remains at the bottom of the reactor with the catalyst) and then water, sorbitol and base were added and the reaction repeated
[b] the catalyst after 2nd reuse and withdrawing of the reaction mixture was 5-times washed with 7 ml (5 × 7 ml) of deionized water It thus will be appreciated that those skilled in the art will be able to devise numerous alternative arrangements that, while not shown or described herein, embody the principles of the invention and thus are within its spirit and scope. This application is not limited to the catalysts, sugar alcohols, bases, polyols, precursors, supports and suspensions as described, but also to their equivalents.

The invention claimed is:

1. A method for hydrogenolysis of sugar or sugar alcohols comprising of the steps of:
   A) mixing in the absence of any phosphine a suspension of a supported catalyst wherein the catalyst consists of osmium metal, water, a sugar or sugar alcohol, and a base,
   B) pressurizing the suspension with hydrogen to a range of about 30 to 90 bar at room temperature,
   C) heating the suspension to a temperature in the range of about 180° C. to 250° C., and
   D) mixing the suspension for an amount of time ranging from about 1 to 6 hours.

2. The method of claim 1, wherein the sugar alcohol is sorbitol.

3. The method of claim 2, in which at least some of the supported catalyst wherein the catalyst consists of osmium metal is recovered and reused for the hydrogenolysis of sugar alcohols.

4. The method of claim 1, wherein the base is selected from the group of alkali metals, alkaline earth metals or mixtures thereof.

5. The method of claim 4, in which at least some of the supported catalyst wherein the catalyst consists of osmium metal is recovered and reused for the hydrogenolysis of sugar alcohols.

6. The method of claim 1, wherein the base is barium hydroxide.

7. The method of claim 6, in which at least some of the supported catalyst wherein the catalyst consists of osmium metal is recovered and reused for the hydrogenolysis of sugar alcohols.

8. The method of claim 1, in which at least some of the supported catalyst wherein the catalyst consists of osmium metal is recovered and reused for the hydrogenolysis of sugar alcohols.

* * * * *